United States Patent [19]
Pang et al.

[11] Patent Number: 5,783,584
[45] Date of Patent: Jul. 21, 1998

[54] THA ANALOGS USEFUL AS CHOLINESTERASE INHIBITORS

[75] Inventors: Yuan-Ping Pang, Ponte Vedra Beach, Fla.; Stephen Brimijoin, Rochester, Minn.

[73] Assignee: Mayo Foundation for Medical Education and Research, Rochester, Minn.

[21] Appl. No.: 570,160

[22] Filed: Dec. 11, 1995

[51] Int. Cl.[6] .................... A61K 31/44; C07D 219/12
[52] U.S. Cl. ................................... 514/297; 546/97
[58] Field of Search ............................ 546/97; 514/297

[56] References Cited

U.S. PATENT DOCUMENTS

| | | | |
|---|---|---|---|
| 4,631,286 | 12/1986 | Shutske et al. | 514/297 |
| 4,816,456 | 3/1989 | Summers | 514/255 |
| 5,026,897 | 6/1991 | Chiang et al. | 560/58 |
| 5,104,880 | 4/1992 | Kozikowski | 514/295 |

FOREIGN PATENT DOCUMENTS

| | | |
|---|---|---|
| 2 264 707 | 9/1993 | United Kingdom. |
| WO 89/02739 | 4/1989 | WIPO. |

OTHER PUBLICATIONS

Teh Kuei Chen, et al., "Diacridines, Bifunctional INtercalators. Chemistry and Antitumor Activity", *J. Med. Chem.*, 21, 868–874, (1978).

Kenneth L. Davis, et al., "Tacrine", *The Lancet*, 345, 625–630, (1995).

Dimitrios Galanakis, et al., "Synthesis and Structure—Activity Relationships of DeQualinium Analogues as K+ Channel Blockers. Investigations on the Role of the Charged Heterocycle", *J. Med. Chem.*, 38, 595–606, (1995).

M. Harel, et al., "Conversion of Acetylcholinesterase to Butyrylcholinesterase: Modeling and Mutagenesis", *Proc. Natl. Acad. Sci. USA*, 89, 10827–10831, (Nov. 1992).

C. M. Himel, et al., "Acidine Araphanes: A New Class of Probe Molecules for Biological Systems", *Science*, 205, 1277–1279, (1979).

Zaven S. Khachaturian, "Diagnosis of Alzheimer's Diseasae", *Arch. Neurol.*, 42, 1097–1105, (1985).

Mark E. Nelson, et al., "9–Aminoacridines Act at a Site Different from that for Mg2+ in Blockade of the N–Methyl–D–Aspartate Receptor Channel", *Mol. Pharmacol.*, 46, 151–160, (1994).

J. Patocka, et al., "Kinetics of Inhibition of Cholinesterases by 1,2,3,4–Tetra–Hydro–9–Aminoacridine in vitro", *Collect. Czech. Chem. Commun.*, 41, 816–824, (1976).

Dennis J. Selkoe, "The Molecular Pathology of Alzheimer's Disease", *Neuron*, 6, 487–498, (1991).

Rudolph Tanzi, et al., "Genetic Heterogeneity of Gene Defects Responsible for Familial Alzheimer's Disease", *Genetica*, 91, 255–263, (1993).

Jeffrey L. Taylor, et al., "Conformers of Acetylcholinesterase: A Mechanism of Allosteric Control", *Mol. Pharmacol.*, 45, 74–83, (1994).

(List continued on next page.)

*Primary Examiner*—Alan L. Rotman
*Attorney, Agent, or Firm*—Schwegman, Lundberg, Woessner & Kluth, P.A.

[57] ABSTRACT

The present invention provides cholinesterase inhibitors of general formula (I):

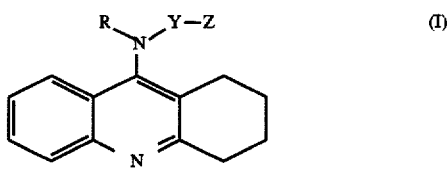

wherein R is H or $(C_1–C_4)$alkyl, Y is a linking group and Z is an alkyl or aryl group, including heteroaryl groups, and the pharmaceutically acceptable salts thereof.

14 Claims, 5 Drawing Sheets

1
a: n=7;
b: n=8;
c: n=9;
d: n=10.

2
a: n=4;   b: n=5;
c: n=6;   d: n=7;
e: n=8;   f: n=9;
g: n=10.

OTHER PUBLICATIONS

I. B. Wilson, et al., "A Power Reactivator of Alkylphosphate-Inhibited Acetylcholinesterase", *Biochim. Biophys. Acta*, 18, 168–170, (1955).

Bindra, J.S., et al., "Synthesis, Pharmacological Activities & Physico-chemical Properties of 4-(Substituted amino/$N^4$-arylpiperazinyl/aminocarbonyl)-2,3-polymethylenequinolines", *Indian Journal of Chemistry*, vol. 26B, pp. 318–329 (Apr. 1987).

Pang, Y., et al., "Highly Potent, Selective, and Low Cost Bis-tetrahydroaminacrine Inhibitors of Acetylcholinesterase", *The Journal of Biological Chemistry*, vol. 271, No. 39, pp. 23646–23649 (Sep. 27, 1996).

Rastogi, S.N., et al., "Local Anaesthetic Activity of 9-Alkylamino-1,2,3,4-Tetrahydroacridines: Structure-Activity Relationship Study", *Indian Journal of Pharmacology*, 19, pp. 44–48 (1987).

Steinberg, G.M., et al., "A Hydrophobic Binding Site in Acetylcholinesterase", *Journal of Medinicinal Chemistry*, vol. 18, No. 11, pp. 1056–1061 (May 12, 1975).

1
a:n=7;
b:n=8;
c:n=9;
d:n=10.

2
a:n=4;  b:n=5;
c:n=6;  d:n=7;
e:n=8;  f:n=9;
g:n=10.

THA ANALOGS USEFUL AS CHOLINESTERASE INHIBITORS

BACKGROUND OF THE INVENTION

Alzheimer's Disease is a devastating neurodegenerative disorder which is characterized by dramatic personality changes and global cognitive decline. It currently affects approximately four million Americans, taking more than 100,000 lives each year. See, R. Tanzi et al., *Genetica*, 91, 255 (1993). As described by D. J. Selkoe, *Neuron*, 6, 487 (1991) and Z. S. Khachaturian, *Arch. Neurol.*, 42, 1097 (1989), this disease is pathologically characterized by the degeneration of the basal forebrain cholinergic system and the deposit of amyloid plaques in the brain.

One approach to treating this disease is to restore the level of neurotransmitter acetylcholine, which is found to be lowered in brains of the Alzheimer's patients, by inhibiting acetylcholinesterase (AChE) with reversible inhibitors. One class of AChE inhibitors includes huperzine A and analogs thereof. See, for example, Kozikowski (U.S. Pat. No. 5,104,880). Another such AChE inhibitor 9-amino-1,2,3,4-tetrahydroacridine (THA, also known as tacrine or COGNEX) is currently a drug approved by the United States Food and Drug Administration for the palliative treatment of mild and moderate Alzheimer's Disease. See, K. L. Davis et al., *Lancet*, 345, 625 (1995). The structure of THA is depicted below.

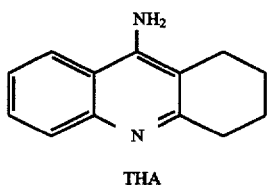

THA

However, the use of THA is currently limited by its serious hepatoxicity. Therefore, there is a continuing need for AChE inhibitors which may be useful to treat Alzheimer's Disease, including analogs of THA exhibiting improved profiles of bioactivity, such as higher potency, and a lower incidence or intensity of side effects.

SUMMARY OF THE INVENTION

The present invention provides cholinesterase inhibitors of the general formula (I):

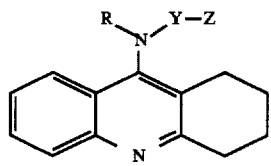

where R is H or $(C_1-C_4)$alkyl, Y is $(C_4-C_{15})$alkylene or $(C_4-C_{15})$alkylene N(R)— and Z is $(C_3-C_{12})$alkyl or a 5–18 membered aryl ring, optionally substituted with CH=NOH and optionally comprising 1–3 N(X), S, non-peroxide O or mixtures thereof, wherein X is absent or is H or $(C_1-C_4)$ alkyl; or a pharmaceutically acceptable salt thereof.

Thus, one embodiment of the present invention provides bioactive THA (tacrine) analogs of the general formula (II):

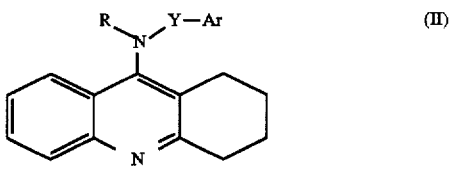

where R is H or $(C_1-C_4)$alkyl, Y is $(C_4-C_{15})$alkylene or $(C_4-C_{15})$alkylene N(R)— and Ar is a 5–18 membered aryl ring, optionally comprising 1–3 N(X), S, non-peroxide O or mixtures thereof, wherein X is absent or is H or $(C_1-C_4)$ alkyl; or a pharmaceutically acceptable salt thereof.

Preferably, R is H or methyl. Y is preferably —$(CH_2)_n$— or —$(CH_2)_n$—N(R)—, wherein n is 4–15, preferably 5–13, most preferably 6–10. Thus, preferred compounds are 1,7-ω-n-alkylene-bis-9,9'-amino- 1,2,3-4-tetrahydroacridines, wherein n is 7–10. The term "aryl ring" includes mono-, bi- and tricyclic ring systems, optionally substituted by CH—NOH, which ring systems comprise at least one aryl ring. Ar is preferably $(C_6-C_{14})$aryl, optionally comprising 1–2 (X)N, i.e., phenyl, indanyl, indanonyl, naphthyl, indenyl, pyridinyl, pyridonyl, or 1,2,3,4-tetrahydroacridine-9-yl. The term "alkyl" as used herein includes straight- and branched-chain alkyl, cycloalkyl, alkyl (cycloalkyl), alkyl(cycloalkyl)alkyl, and (cycloalkyl)(alkyl), optionally comprising 1–2 N(X), S, or O and/or 1–3 double bonds. The term "cycloalkyl" also includes bicyclo-, tricyclo- and tetracycloalkyl. Z is preferably a secondary or tertiary alkyl group such as isopropyl, t-butyl, or 3-pentyl, which may contain further branching, or cycloalkyl such as cyclopentyl, cyclohexyl, norbornyl, or adamantyl.

The compounds of formula (I), particularly those of formula (II), were found to be up to about 7,000-fold more selective and 1,000-fold more potent in reversably inhibiting AChE than THA. Thus, the present compounds are useful (i) to evaluate the role of AChE inhibition by THA in treating Alzheimer's Disease, (ii) as potential, prophylactic or therapeutic antidotes for chemical warfare agents and for organophosphate insecticides (i.e., organophosphate poisoning) (see, P. X. Chiang et al., U.S. Pat. No. 5,026,897); (iii) as potential drugs for killing parasites, (iv) as insecticides (see Wilson et al., *Biochim. Biophys. Acta.*, 18, 168 (1955)), (v) as potential blockers of $K^+$ channel and the N-methyl-D-aspartate receptor channel (see J. Patocka et al., *Collect. Czech. Chem. Commun.*, 41, 816 (1976); D. Galanakis et al., *J. Med. Chem.*, 38, 595 (1995) and M. E. Nelson et al., *Mol. Pharmacol.*, 46, 151 (1994)); (vi) as therapeutic agents for the treatment of Alzheimer's Disease and other neurological conditions which can be ameliorated by the inhibition of AChE activity and/or BChE activity in a mammal such as a human, afflicted with said condition, and (vii) as reversible, selective, and potent butyrylcholinesterase (BChE) inhibitors to affect alterations in the permissive or causative role BChE in the neuropathology of AD or other dementing illness.

Thus, the present invention also provides pharmaceutical, parasiticidal or insecticidal compositions comprising an effective amount of one or more compounds of formula (I) in combination with an acceptable carrier vehicle for a pharmaceutical, parasiticidal, or insecticidal composition.

DETAILED DESCRIPTION OF THE INVENTION

Figure 1:
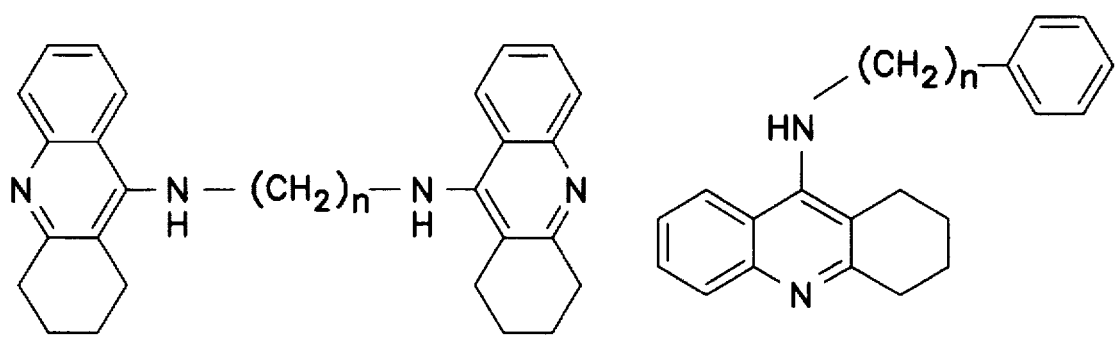
FIG. 1 depicts the structures of analogs 1a–d and 2a–g.
Figure 2:
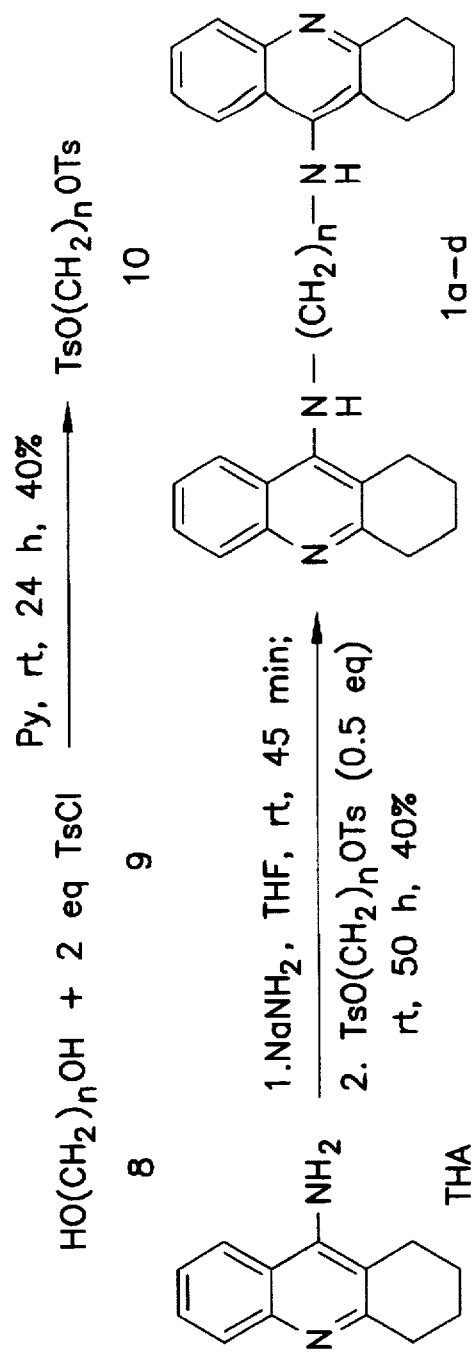
FIG. 2 schematically depicts the synthesis of ditosylate 10 and THA analogs 1a–d.

Analogs (1a–d) were readily prepared as shown in FIG. 2. The commercially available 1,ω-alkanediol (n=7–10) was first converted to bistosylate in about 40% yield by reacting the alcohol with two equivalents of tosyl chloride in pyridine. The bis-tosylate was then reacted at room temperature with two equivalents of THA anion, prepared by reacting THA in its base form with sodium amide, to yield the designed analog in series 1.

Figure 3:
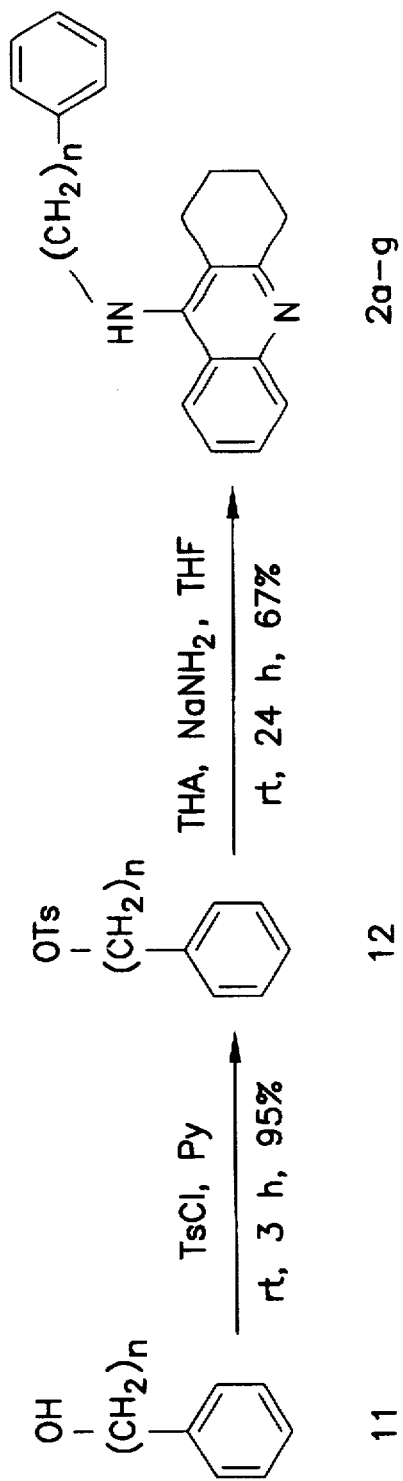
FIG. 3 schematically depicts the synthesis of analogs 2a–g.
Figure 4:
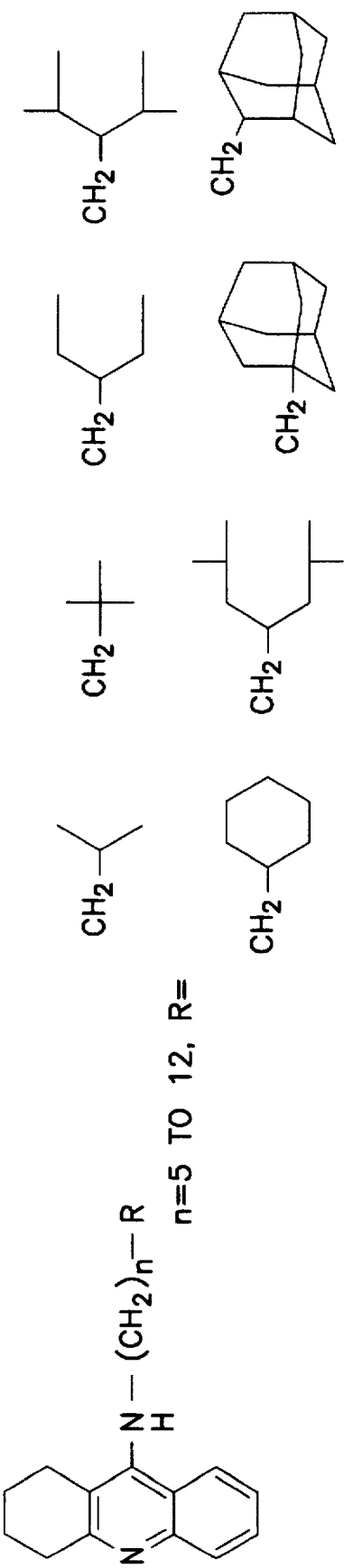
FIG. 4 depicts structures of analogs of formula (I) wherein Z is alkyl.

Analogs (2a–g) were prepared according to FIG. 3. The commercially available N-phenyl-1-alkyl alcohol (n=4–10) was first converted to tosylate in about 95% yield by reacting the alcohol with tosyl chloride in pyridine. The tosylate was then reacted at room temperature with one equivalent of the THA anion prepared as above to yield the desired analog.

One of ordinary skill in the art can readily prepare other analogs of formula (I) by substituting compounds of general formula TsO—Y—Ar or TsO—Y—Alkyl for compound 12 in FIG. 3. The aryl group (Ar) is as defined above, e.g., Ar can be a $C_6$–$C_{18}$, aryl moiety, such as phenyl, naphthyl, 1,2,3,4-tetrahydronaphthyl, or a heteroaryl, i.e. a heteroaromatic ring system, such as pyridine, furan, thiophene, pyrrole, acridine, 1,2,3,4-tetrahydroacridine, imidazole, pyrazole, oxazole, isoxazole, indole, indanyl, benzofuran, benzothiophene, quinoline, isoquinoline, carbazole, isothiazole, thiazole, pyridazine, pyrimidine, or pyrazine, and the like.

Mono-substituted amino compounds of formula I, wherein R is ($C_1$–$C_4$)alkyl, aryl, or aralkyl can be prepared by conventional methods for the conversion of secondary amino groups to tertiary amino groups. For example, see I. T. Harrison et al., *Compendium of Organic Synthetic Methods*, Wiley-Interscience, N.Y. (1971) at pages 240–246.

The oxime substituted compounds of formula (I) can be prepared by converting the carbonyl group, which should be protected in the reaction of coupling to the THA moiety, of the indanone derivatives to an oxime group. See, I. T. Harrison et al., *Compendium*, cited above, at page 235; *J. Biol. Chem.*, 211, 725 (1954); *J. Amer. Chem. Soc.*, 50, 3370 (1928).

Pharmaceutically acceptable acid salts of the present compounds can be prepared as described in U.S. Pat. No. 4,383,114.

The compounds of formula I can be employed, singly or in combination, in an amount effective to inhibit the cholinesterase enzymes (such as BChE or AChE) in an insect or a mammal (such as a human). Therefore, the present invention also includes a pharmaceutical composition, such as one or more unit dosage forms, of an effective cholinesterase enzyme-inhibiting amount of one or more of the compounds of formula I in combination with a pharmaceutically acceptable carrier therefor. Such therapeutic compositions can be administered orally or parenterally, including via intravenous, intramuscular, intraperitoneal, subcutaneous, or topical administration.

For oral use of a compound of general formula I, said compound can be administered, for example, in the form of tablets or capsules, or as an aqueous solution or suspension. In the case of tablets for oral use, carriers which are commonly used include lactose, mannitol and corn starch, and lubricating agents, such as magnesium stearate, are commonly added. For oral administration in capsule form, the compound can be administered in dry form in a hard gelatin capsule or in a suitable gelled or liquid vehicle, such as a liquid polyethylene glycol or a carrageenan gel, in a soft gelatin capsule. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous infusion or injection, the total concentration of solutes should be controlled in order to render the preparations isotonic.

When a compound according to general formula I is used as in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.05 mg/kg to about 25 mg/kg of body weight, and preferably, of from 0.1 mg/kg to about 10 mg/kg of body weight, administered in single or divided doses. In some cases, however, it may be necessary to use dosages outside these limits. Useful dosages may be calculated, to some extent, or those found to be effective when other AChE inhibitors, such as huperzine A, are administered to animals or humans. See, for example, C. Tang et al., *Acta Pharmacol. Sinica*, 7, 507 (1986); G. P. Vincent et al., *Neurosci Abstr.* 13, 884 (1987); and Y. -S. Cheng, *New Drugs and Clinical Remedies*, 5, 197 (1986).

For insecticidal or parasiticidal uses, the compounds of the invention can be coated, sprayed, or dusted onto the target surface as compositions comprising suitable carriers, such as inert powdered solids or liquids, optionally containing surfactants, dispersing agents, and other adjuvants.

The invention will be further described by reference to the following detailed examples, wherein tetrahydrofuran (THF) was distilled from sodium benzophenone ketyl prior to use. Solvents used for chromatography were purchased in 5-gal drums. Silica gel 60 (Merck, 230–400 mesh ASTM for flash chromatography) was used for column chromatography. TLC was performed on Merck silica gel 60F-254 (0.25 mm, precoated on glass). Other reagents were used as supplied by the Aldrich Chemical Co. and Lancaster Synthesis Inc.

Chemical shifts are reported in delta units with reference to $(CH_3)_4Si$ (δ=0.00 ppm) for $^1H$ or $CDCl_3$ (δ=77.00 ppm) for $^{13}C$ as internal standards.

EXAMPLE 1

Toluene-4-sulfonic Acid 7-Toluene-4-sulfonyloxyheptyl Ester

Pyridine (7 mL) was added to 4326 mg (22.7 mmol) of p-toluenesulfonyl chloride at room temperature under $N_2$. The color of the solution changed immediately to yellow after addition. 1,7-heptanediol (1000 mg, 7.6 mmol) in 7 mL of pyridine was then added dropwise to the solution at 0° C. The resulting solution was stirred at 0° C. for 30 minutes, slowly warmed to room temperature, and then stirred at room temperature for 24 hours. White precipitates were generated and the color of the solution turned to brownish. The tosylate was extracted with $CHCl_3$ and washed with saturated $NH_4Cl$. Flash chromatography on silica gel eluting with 30% EtOAc in hexane yielded 1332 mg (40%) of the tosylate as white crystals: $^1H$ NMR ($CDCl_3$, 300 Mz) δ 7.79 (d, J=9.0 Hz, 4 H), 7.35 (d, J=9.0 Hz, 4 H), 3.99 (t, J=6.0 Hz, 4 H), 2.45 (s, 6 H), 1.68–1.54 (m, 4 H), 1.36–1.18 (m, 6 H); $^{13}C$ NMR ($CDCl_3$, 75.46 MHz) δ 144.60, 132.80, 129.66, 127.59, 70.32, 28.37, 27.95, 24.88, 21.39.

EXAMPLE 2

Toluene-4-sulfonic Acid 8-Toluene-4-sulfonyloxy-octyl Ester

The same procedure as employed in the preparation of toluene-4-sulfonic acid 7-toluene-4-sulfonyloxy-heptyl ester was followed to afford the product as white crystals: H NMR ($CDCl_3$, 300 MHz) δ 7.79 (d, J=9.0 Hz, 4 H), 7.35 (d, J=9.0 Hz, 4 H), 4.00 (t, J=6.0 Hz, 4 H), 2.45 (s, 6 H), 1.68–1.58 (m, 4 H), 1.38–1.16 (m, 8 H); $^{13}C$ NMR ($CDCl_3$, 75.46 MHz) δ 144.65, 133.05, 129.76, 127.78, 70.50, 28.64, 28.57, 25.10, 21.56.

EXAMPLE 3

Toluene-4-sulfonic Acid 9-Toluene-4-sulfonyloxy-nonyl Ester

The same procedure as employed in the preparation of toluene-4-sulfonic acid 7-toluene-4-sulfonyloxy-heptyl ester was followed to afford the product as white crystals: $^1H$ NMR ($CDCl_3$, 300 MHz) δ 7.79 (d, J=9.0 Hz, 4 H), 7.35 (d, J=9.0 Hz, 4 H), 4.01 (t, J=6.0 Hz, 4 H), 2.45 (s, 6 H), 1.78–1.58 (m, 4 H), 1.36–1.18 (m, 10 H); $^{13}C$ NMR ($CDCl_3$, 75.46 MHz) δ 144.58, 132.93, 129.69, 127.67, 70.53, 28.90, 28.56, 25.08, 21.45.

EXAMPLE 4

Toluene-4-sulfonic Acid 10-Toluene-4-sulfonyloxy-decyl Ester

The same procedure as employed in the preparation of toluene-4-sulfonic acid 7-toluene-4-sulfonyloxy-heptyl ester was followed to afford the product as white crystals: $^1H$ NMR ($CDCl_3$, 300 MHz) δ 7.79 (d, J=9.0 Hz, 4 H), 7.35 (d, J=9.0 Hz, 4 H), 4.01 (t, J=6.0 Hz, 4 H), 2.45 (s, 6 H), 1.68–1.58 (m, 4 H), 1.35–1.16 (m, 12 H); $^{13}C$ NMR ($CDCl_3$, 75.46 MHz) δ 144.60, 133.10, 129.74, 127.78, 70.61, 29.10, 28.74, 25.21, 21.56.

EXAMPLE 5

1-7-n-Heptylene-bis-9,9'-amino-1,2,3,4-tetrahydroacridine (1a)

A solution of 1015 mg (5.1 mmol) of THA in 4 mL of THF was added to the suspension of 240 mg (6.2 mmol) of $NaNH_2$ in 4 mL of THF under $N_2$. The mixture was vigorously stirred at room temperature for 45 minutes. A solution of 749 mg (1.7 mmol) of toluene-4-sulfonic acid 7-toluene-4-sulfonyloxy-heptyl ester in 8 mL of THF was then added to the orange-red mixture and kept stirring at room temperature for 50 hours. The product was extracted with EtOAc and washed with saturated $Na_2CO_3$. Flash chromatography on $NH_3$ saturated silica gel eluting with 5% methanol in $CHCl_3$ afforded 318 mg (38%) of the product as a yellow oil: IR ($CDCl_3$) 3347, 3061, 2932, 2859, 2180, 1615, 1580, 1562, 1499, 1420, 1358, 1296, 1273, 1167, 1130, 941, 909, 762, 731, 679, 640 $cm^{-1}$; $^1H$ NMR ($CDCl_3$, 300 MHz) δ 7.94 (d, J=9.0 Hz, 2 H), 7.90 (d, J=9.0 Hz, 2 H), 7.55 (t, J=8.0 Hz, 2 H), 7.34 (t, J=5.0 Hz, 2 H), 3.91 (s, 2 H), 3.54–3.38 (m, 4 H), 3.11–2.99 (m, 4 H), 2.78–2.66 (m, 4 H), 1.99–1.85 (m, 8 H), 1.71–1.57 (m, 4 H), 1.46–1.31 (m, 6 H); $^{13}C$ NMR ($CDCl_3$, 75.46 MHz) δ 158.35, 150.49, 147.40, 128.65, 128.04, 123.38, 122.65, 120.11, 115.79, 49.25, 33.96, 31.52, 28.95, 26.67, 24.65, 22.90, 22.65.

EXAMPLE 6

1-8-n-Octylene-bis-9,9'-amino-1,2,3,4-tetrahydroacridine (1b)

The same procedure as employed in the preparation of 1-7-n-heptylene-bis-9,9'-amino-1,2,3,4-tetrahydroacridine was followed to afford the product as a yellow oil: IR ($CDCl_3$) 3347, 3063, 2932, 2857, 2182, 1615, 1582, 1564, 1503, 1420, 1360, 1298, 1273, 1130, 939, 909, 762, 731, 640 $cm^{-1}$; $^1H$ NMR ($CDCl_3$, 300 MHz) δ 7.95 (d, J=9.0 Hz, 2 H), 7.90 (d, J=9.0 Hz, 2 H), 7.55 (t, J=8.0 Hz, 2 H), 7.34 (t, J=5.0 Hz, 2 H), 3.92 (s, 2 H), 3.47 (t, J=8.0 Hz, 4 H), 3.11–2.99 (m, 4 H), 2.78–2.66 (m, 4 H), 2.00–1.83 (m, 8 H), 1.71–1.54 (m, 4 H), 1.45–1.21 (m, 8 H); $^{13}C$ NMR ($CDCl_3$, 75.46 MHz) δ 158.38, 150.55, 147.45, 128.70, 128.06, 123.40, 122.70, 120.14, 115.79, 49.34, 34.00, 31.60, 29.12, 26.69, 24.68, 22.95, 22.70.

EXAMPLE 7

1-9-n-Nonylene-bis-9,9'-amino-1,2,3,4-tetrahydroacridine (1c)

The same procedure as employed in the preparation of 1-7-n-heptylene-bis-9,9'-amino-1,2,3,4-tetrahydroacridine was followed to afford the product as a yellow oil: IR ($CDCl_3$) 3356, 3063, 2930, 2857, 2182, 1615, 1582, 1564, 1505, 1418, 1360, 1298, 1273, 1130, 909, 762, 731, 681, 640 $cm^{-1}$; $^1H$ NMR ($CDCl_3$, 300 MHz) δ 7.95 (d, J=9.0 Hz, 2 H), 7.90 (d, J=9.0 Hz, 2 H), 7.55 (t, J=8.0 Hz, 2 H), 7.34 (t, J=5.0 Hz, 2 H), 3.93 (s, 2 H), 3.47 (t, J=6.0 Hz, 4 H), 3.11–2.99 (m, 4 H), 2.78–2.66 (m, 4 H), 1.99–1.85 (m, 8 H), 1.73–1.55 (m, 4 H), 1.44–1.21 (m, 10 H); $^{13}C$ NMR ($CDCl_3$, 75.46 MHz) δ 158.32, 150.54, 147.42, 128.64, 128.01, 123.35, 122.68, 120.11, 115.71, 49.31, 33.95, 31.60, 29.23, 29.08, 26.72, 24.64, 22.92, 22.66.

EXAMPLE 8

1-10-n-Decylene-bis-9,9'-amino-1,2,3,4-tetrahydroacridine (1d)

The same procedure as employed in the preparation of 1-7-n-heptylene-bis-9,9'-amino-1,2,3,4-tetrahydroacridine was followed to afford the product as a yellow oil: IR ($CDCl_3$) 3345, 3063, 2928, 2855, 2182, 1615, 1582, 1564, 1503, 1420, 1360, 1296, 1169, 1130, 941, 909, 762, 731, 679 $cm^{-1}$; $^1H$ NMR ($CDCl_3$, 300 MHz) δ 7.96 (d, J=9.0 Hz, 2 H), 7.90 (d, J=9.0 Hz, 2 H), 7.55 (t, J=8.0 Hz, 2 H), 7.34 (t, J=5.0 Hz, 2 H), 3.93 (s, 2 H), 3.47 (t, J=8.0 Hz, 4 H), 3.11–2.99 (m, 4 H), 2.78–2.66 (m, 4 H), 1.99–1.85 (m, 8 H), 1.72–1.55 (m, 4 H), 1.44–1.22 (m, 12 H); $^{13}C$ NMR ($CDCl_3$, 75.46 MHz) δ 158.34, 150.60, 147.44, 128.65, 128.06, 123.38, 122.73, 120.12, 115.71, 49.38, 33.97, 31.65, 29.28, 29.18, 26.78, 24.67, 22.95, 22.70.

EXAMPLE 9

Toluene-4-sulfonic Acid 4-Phenyl-butyl Ester

Pyridine (10 mL) was added to 1487 mg (7.8 mmol) of p-toluenesulfonyl chloride at room temperature under $N_2$.

The color of the solution changed immediately to yellow after addition. 4-Phenyl-1-butanol (781 mg, 5.2 mmol) was then added dropwise to the solution. The resulting solution was stirred at room temperature for three hours. White precipitates were generated and the color of the solution turned to brownish. The tosylate was extracted with EtOAc and washed with saturated $NH_4Cl$. Flash chromatography on silica gel eluting with 10% EtOAc in hexane yielded 1503 mg (95%) of the tosylate as a colorless oil: IR ($CDCl_3$) 3061, 3028, 2945, 2861, 1923, 1807, 1659, 1599, 1495, 1454, 1360, 1308, 1292, 1177, 1098, 1018, 936, 816 $cm^{-1}$; $^1H$ NMR ($CDCl_3$, 300 MHz) δ 7.78 (d, J=9.0 Hz, 2 H), 7.33 (d, J=6.0 Hz, 2 H), 7.28–7.24 (m, 2 H), 7.20–7.15 (m, 1 H), 7.10 (d, J=6.0 Hz, 2 H), 4.03 (t, J=6.0 Hz, 2 H), 2.56 (t, J=6.0 Hz, 2 H), 2.44 (s, 3 H), 1.74–1.57 (m, 4 H); $^{13}C$ NMR ($CDCl_3$, 75.46 MHz) δ 144.51, 141.31, 132.81, 129.63, 128.09, 127.56, 125.64, 70.22, 34.78, 28.03, 26.81, 21.34.

EXAMPLE 10

Toluene-4-sulfonic Acid 5-Phenyl-pentyl Ester

The same procedure as employed in the preparation of toluene-4-sulfonic acid 4-phenyl-butyl ester was followed to afford the product as a colorless oil: IR ($CDCl_3$) 3063, 3027, 2938, 2859, 1923, 1807, 1599, 1495, 1454, 1358, 1175, 1098, 1030, 947, 910, 814, 748, 700, 664 $cm^{-1}$; $^1H$ NMR ($CDCl_3$, 300 MHz) δ 7.78 (d, J=9.0 Hz, 2 H), 7.33 (d, J=9.0 Hz, 2 H), 7.29–7.24 (m, 2 H), 7.20–7.17 (m, 1 H), 7.12 (d, J=6.0 Hz, 2 H), 4.01 (t, J=6.0 Hz, 2 H), 2.56 (t, J=8.0 Hz, 2 H), 2.44 (s, 3 H), 1.71–1.62 (m, 2 H), 1.59–1.51 (m, 2 H), 1.39–1.31 (m, 2 H); $^{13}C$ NMR ($CDCl_3$, 75.46 MHz) δ 144.35, 141.78, 132.76, 129.51, 127.95, 127.90, 127.43, 126.98, 125.36, 70.17, 35.23, 30.31, 28.25, 24.57, 21.17.

EXAMPLE 11

Toluene-4-sulfonic Acid 6-Phenyl-hexyl Ester

The same procedure as employed in the preparation of toluene-4-sulfonic acid 4-phenyl-butyl ester was followed to afford the product as a colorless oil: IR ($CDCl_3$) 3061, 3027, 2932, 2857, 2361, 2342, 1599, 1495, 1454, 1360, 1177, 1098, 959, 918, 816, 748, 700, 665 $cm^{-1}$; $^1H$ NMR ($CDCl_3$, 300 MHz) δ 7.78 (d, J=9.0 Hz, 2 H), 7.34 (d, J=9.0 Hz, 2 H), 7.29–7.25 (m, 2 H), 7.19–7.13 (m, 3 H), 4.01 (t, J=6.0 Hz, 2 H), 2.56 (t, J=8.0 Hz, 2 H), 2.44 (s, 3 H), 1.65–1.54 (m, 4 H), 1.36–1.23 (m, 4 H); $^{13}C$ NMR ($CDCl_3$, 75.46 MHz) δ 144.40, 142.15, 132.86, 129.55, 128.03, 127.95, 127.51, 125.35, 70.34, 35.42, 30.87, 28.39, 28.20, 24.88, 21.26.

EXAMPLE 12

Toluene-4-sulfonic Acid 7-Phenyl-heptyl Ester

The same procedure as employed in the preparation of toluene-4-sulfonic acid 4-phenyl-butyl ester was followed to afford the product as a colorless oil: IR ($CDCl_3$) 3061, 3027, 2930, 2857, 1599, 1495, 1454, 1360, 1177, 1098, 1020, 961, 930, 816, 748, 700, 664, 575, 556 $cm^{-1}$; $^1H$ NMR ($CDCl_3$, 300 MHz) δ 7.78 (d, J=9.0 Hz, 2 H), 7.33 (d, J=6.0 Hz, 2 H), 7.29–7.25 (m, 2 H), 7.19–7.14 (m, 3 H), 4.01 (t, J=6.0 Hz, 2 H), 2.57 (t, J=8.0 Hz, 2 H), 2.44 (s, 3 H), 1.65–1.52 (m, 4 H), 1.39–1.21 (m, 6 H); $^{13}C$ NMR ($CDCl_3$, 75.46 MHz) δ 144.47, 142.43, 132.99, 129.62, 128.15, 128.03, 127.62, 125.41, 70.45, 35.64, 31.09, 28.77, 28.54, 25.04, 21.37.

EXAMPLE 13

Toluene-4-sulfonic Acid 8-Phenyl-octyl Ester

The same procedure as employed in the preparation of toluene-4-sulfonic acid 4-phenyl-butyl ester was followed to afford the product as a colorless oil: IR ($CDCl_3$) 3061, 3027, 2926, 2855, 1923, 1807, 1655, 1599, 1495, 1454, 1358, 1306, 1292, 1177, 1098, 1030, 941, 814, 748, 700, 664 $cm^{-1}$; $^1H$ NMR ($CDCl_3$, 300 MHz) δ 7.79 (d, J=9.0 Hz, 2 H), 7.33 (d, J=6.0 Hz, 2 H), 7.27–7.25 (m, 2 H), 7.19–7.15 (m, 3 H), 4.01 (t, J=6.0 Hz, 2 H), 2.58 (t, J=8.0 Hz, 2 H), 2.44 (s, 3 H), 1.64–1.55 (m, 4 H), 1.35–1.20 (m, 8 H); $^{13}C$ NMR ($CDCl_3$, 75.46 MHz) δ 144.47, 142.55, 133.01, 129.64, 128.18, 128.04, 127.66, 125.41, 70.50, 35.73, 31.23, 29.04, 28.91, 28.60, 25.10, 21.41.

EXAMPLE 14

Toluene-4-sulfonic Acid 9-Phenyl-nonyl Ester

The same procedure as employed in the preparation of toluene-4-sulfonic acid 4-phenyl-butyl ester was followed to afford the product as a colorless oil: IR ($CDCl_3$) 3063, 3027, 2928, 2855, 1599, 1495, 1454, 1360, 1177, 953, 916, 816, 748, 700, 664, 577, 556 $cm^{-1}$; $^1H$ NMR ($CDCl_3$, 300 MHz) δ 7.79 (d, J=9.0 Hz, 2 H), 7.34 (d, J=9.0 Hz, 2 H), 7.30–7.25 (m, 2 H), 7.19–7.16 (m, 3 H), 4.01 (t, J=6.0 Hz, 2 H), 2.59 (t, J=8.0 Hz, 2 H), 2.44 (s, 3 H), 1.65–1.57 (m, 4 H), 1.35–1.17 (m, 10 H); $^{13}C$ NMR ($CDCl_3$, 75.46 MHz) δ 144.49, 142.68, 133.08, 129.68, 128.23, 128.09, 127.71, 125.44, 70.56, 35.81, 31.34, 29.15, 29.09, 28.75, 28.64, 25.16, 21.47.

EXAMPLE 15

Toluene-4-sulfonic Acid 10-Phenyl-decyl Ester

The same procedure as employed in the preparation of toluene-4-sulfonic acid 4-phenyl-butyl ester was followed to afford the product as a colorless oil: IR ($CDCl_3$) 3061, 3027, 2926, 2855, 1921, 1805, 1653, 1599, 1495, 1454, 1360, 1306, 1292, 1177, 1098, 1020, 959, 928, 816 $cm^{-1}$; $^1H$ NMR ($CDCl_3$, 300 MHz) δ 7.79 (d, J=9.0 Hz, 2 H), 3.34 (d, J=9.0 Hz, 2 H), 7.30–7.25 (m, 2 H), 7.18–7.16 (m, 3 H), 4.01 (t, J=6.0 Hz, 2 H), 2.59 (t, J=8.0 Hz, 2 H), 2.44 (s, 3 H), 1.65–1.57 (m, 4 H), 1.28–1.21 (m, 12 H); $^{13}C$ NMR ($CDCl_3$, 75.46 MHz) δ 144.52, 142.79, 133.20, 129.71, 128.31, 128.14, 127.79, 125.47, 70.62, 35.89, 31.41, 29.33, 29.26, 29.20, 28.81, 28.73, 25.24, 21.53.

EXAMPLE 16

(4-Phenyl-butyl)-(1,2,3,4-tetrahydro-acridine-9-yl)-amine (2a)

A solution of 458 mg (2.3 mmol) of THA in 5 mL of THF was added to the suspension of 180 mg (4.6 mmol) of $NaNH_2$ in 2 mL of THF under $N_2$. The mixture was vigorously stirred at room temperature for 45 minutes. A solution of 700 mg (2.3 mmol) of toluene-4-sulfonic acid 4-phenyl-butyl ester in 14 mL of THF was then added to the orange-red mixture and kept stirring at room temperature for 24 hours. The product was extracted with EtOAc and washed with saturated $Na_2CO_3$. Flash chromatography on $NH_3$ saturated silica gel eluting with 30% EtOAc in hexane afforded 509 mg (67%) of the product as a yellow oil: IR ($CDCl_3$) 3351, 3061, 3025, 2934, 2859, 1655, 1615, 1582, 1562, 1497, 1452, 1420, 1362, 1333, 1142, 943, 856, 762, 700 $cm^{-1}$; $^1H$ NMR ($CDCl_3$, 300 MHz) δ 7.91 (t, J=9.0 Hz, 2 H), 7.55–7.52 (m, 1 H), 7.36–7.26 (m, 3 H), 7.21–7.14 (m, 3 H), 3.89 (s, 1 H), 3.49 (t, J=8.0 Hz, 2 H), 3.11–2.99 (m, 2 H), 2.70–2.56 (m, 4 H), 1.96–1.87 (m, 4 H), 1.77–1.67 (m, 4 H); $^{13}C$ NMR ($CDCl_3$, 75.46 MHz) δ 158.34, 150.48, 147.42, 141.73, 128.68, 128.20, 128.06, 125.74, 123.43, 122.65, 120.17, 115.90, 49.13, 35.39, 33.97, 31.10, 28.53, 24.63, 22.90, 22.66.

EXAMPLE 17

(5-Phenyl-pentyl)-(1,2,3,4-tetrahydro-acridine-9-yl)-amine (2b)

The same procedure as employed in the preparation of (4-phenyl-butyl)-(1,2,3,4-tetrahydro-acridine-9-yl)-amine was followed to afford the product as a yellow oil: IR (CDCl$_3$) 3347, 3061, 3025, 2932, 2857, 1615, 1603, 1562, 1497, 1452, 1420, 1358, 1298, 1125, 939, 909, 762, 700 cm$^{-1}$; $^1$H NMR (CDCl$_3$, 300 MHz) δ 7.91 (t, J=9.0 Hz, 2 H), 7.59–7.50 (m, 1 H), 7.36–7.25 (m, 3 H), 7.20–7.14 (m, 3 H), 3.90 (s, 1 H), 3.54–3.42 (m, 2 H), 3.10–2.98 (m, 2 H), 2.69–2.59 (m, 4 H), 1.93–1.90 (m, 4 H), 1.71–1.61 (m, 4 H), 1.47–1.39 (m, 2 H); $^{13}$C NMR (CDCl$_3$, 75.46 MHz) δ 158.17, 150.32, 147.34, 141.92, 128.57, 128.06, 128.01, 127.87, 125.46, 123.23, 122.59, 120.00, 115.60, 49.06, 35.45, 33.89, 31.30, 30.78, 26.16, 24.48, 22.79, 22.54.

EXAMPLE 18

(6-Phenyl-hexyl)-(1,2,3,4-tetrahydro-acridine-9-yl)-amine (2c)

The same procedure as employed in the preparation of (4-phenyl-butyl)-(1,2,3,4-tetrahydro-acridine-9-yl)-amine was followed to afford the product as a yellow oil: IR (CDCl$_3$) 3345, 3061, 3025, 2930, 2857, 1615, 1582, 1562, 1497, 1454, 1420, 1360, 1298, 1125, 941, 909, 762, 698 cm$^{-1}$; $^1$H NMR (CDCl$_3$, 300 MHz) δ 7.92 (dd, J=9.0, 15.0 Hz, 2 H), 7.60–7.50 (m, 1 H), 7.36–7.25 (m, 3 H), 7.20–7.15 (m, 3 H), 3.92 (s, 1 H), 3.49–3.45 (m, 2 H), 3.11–3.01 (m, 2 H), 2.77–2.65 (m, 2 H), 2.60 (t, J=8.0 Hz, 2 H), 1.96–1.90 (m, 4 H), 1.67–1.58 (m, 4 H), 1.48–1.35 (m, 4 H); $^{13}$C NMR (CDCl$_3$, 75.46 MHz) δ 158.33, 150.51, 147.47, 142.35, 128.71, 128.20, 128.11, 128.04, 125.52, 123.37, 122.69, 120.14, 115.74, 49.32, 35.66, 34.01, 31.55, 31.16, 28.81, 26.67, 24.66, 22.94, 22.69.

EXAMPLE 19

(7-Phenyl-heptyl)-(1,2,3,4-tetrahydro-acridine-9-yl)-amine (2d)

The same procedure as employed in the preparation of (4-phenyl-butyl)-(1,2,3,4-tetrahydro-acridine-9-yl)-amine was followed to afford the product as a yellow oil: IR (CDCl$_3$) 3347, 3061, 3025, 2930, 2855, 1615, 1603, 1562, 1497, 1454, 1420, 1360, 1123, 1028, 943, 762, 698 cm$^{-1}$; $^1$H NMR (CDCl$_3$, 300 MHz) δ 7.92 (dd, J=9.0, 15.0 Hz, 2 H), 7.54 (t, J=8.0 Hz, 1 H), 7.36–7.19 (m, 3 H), 7.17–7.15 (m, 3 H), 3.92 (s, 1 H), 3.49–3.46 (m, 2 H), 3.11–2.99 (m, 2 H), 2.78–2.66 (m, 2 H), 2.59 (t, J=8.0 Hz 2 H), 1.94–1.90 (m, 4 H), 1.67–1.58 (m, 4 H), 1.41–1.33 (m, 6 H); $^{13}$C NMR (CDCl$_3$, 75.46 MHz) δ 158.33, 150.54, 147.50, 142.51, 128.73, 128.21, 128.09, 125.47, 123.35, 122.71, 120.14, 115.71, 49.35, 35.75, 34.03, 31.62, 31.21, 29.09, 28.98, 26.72, 24.65, 22.95, 22.70.

EXAMPLE 20

(8-Phenyl-octyl)-(1,2,3,4-tetrahydro-acridine-9-yl)-amine (2e)

The same procedure as employed in the preparation of (4-phenyl-butyl)-(1,2,3,4-tetrahydro-acridine-9-yl)-amine was followed to afford the product as a yellow oil: IR (CDCl$_3$) 3354, 3061, 3025, 2928, 2855, 1615, 1582, 1562, 1497, 1454, 1420, 1358, 1296, 1273, 1121, 1028, 943, 909, 760, 698 cm$^{-1}$; $^1$H NMR (CDCl$_3$, 300 MHz) δ 7.92 (dd, J=9.0, 15 Hz, 2 H), 7.60–7.50 (m, 1 H), 7.36–7.24 (m, 3 H), 7.19–7.15 (m, 3 H), 3.92 (s, 1 H), 3.49–3.42 (m, 2 H), 3.06–3.04 (m, 2 H), 2.78–2.66 (m, 2 H), 2.59 (t, J=9.0 Hz, 2 H), 1.94–1.87 (m, 4 H), 1.67–1.58 (m, 4 H), 1.40–1.31 (m, 8 H); $^{13}$C NMR (CDCl$_3$, 75.46 MHz) δ 158.46, 150.68, 147.56, 142.73, 128.79, 128.32, 128.17, 125.53, 123.47, 122.80, 120.23, 115.83, 49.50, 35.89, 34.10, 31.74, 31.38, 29.32, 29.23, 29.12, 26.87, 24.75, 23.04, 22.79.

EXAMPLE 21

(9-Phenyl-nonyl)-(1,2,3,4-tetrahydro-acridine-9-yl)-amine (2f)

The same procedure as employed in the preparation of (4-phenyl-butyl)-(1,2,3,4-tetrahydro-acridine-9-yl)-amine was followed to afford the product as a yellow oil: IR (CDCl$_3$) 3354, 3061, 3027, 2928, 2855, 2180, 1615, 1582, 1564, 1497, 1454, 1418, 1360, 1298, 1121, 941, 909, 760, 698 cm$^{-1}$; $^1$H NMR (CDCl$_3$, 300 MHz) δ 7.93 (dd, J=9.0, 18.0 Hz, 2 H), 7.60–7.49 (m, 1 H), 7.36–7.25 (m, 3 H), 7.19–7.16 (m, 3 H), 3.92 (s, 1 H), 3.49–3.45 (m, 2 H), 3.06–3.04 (m, 2 H), 2.76–2.65 (m, 2 H), 2.59 (t, J=8.0 Hz, 2 H), 1.94–1.90 (m, 4 H), 1.67–1.58 (m, 4 H), 1.40–1.29 (m, 10 H); $^{13}$C NMR (CDCl$_3$, 75.46 MHz) δ 158.18, 150.46, 147.38, 142.54, 128.59, 128.12, 127.95, 125.31, 123.23, 122.65, 120.03, 115.55, 49.25, 35.72, 33.91, 31.52, 31.24, 29.19, 29.14, 29.01, 26.67, 24.54, 22.84, 22.59.

EXAMPLE 22

(10-Phenyl-decyl)-(1,2,3,4-tetrahydro-acridine-9-yl)-amine (2g)

The same procedure as employed in the preparation of (4-phenyl-butyl)-(1,2,3,4-tetrahydro-acridine-9-yl)-amine was followed to afford the product as a yellow oil: IR (CDCl$_3$) 3370, 3061, 3025, 2926, 2855, 1657, 1582, 1562, 1497, 1454, 1420, 1362, 1123, 762, 698 cm$^{-1}$; $^1$H NMR (CDCl$_3$, 300 MHz) δ 7.93 (dd, J=9.0, 18.0 Hz, 2 H), 7.60–7.50 (m, 1 H), 7.37–7.25 (m, 3 H), 7.19–7.14 (m, 3 H), 3.93 (s, 1 H), 3.54–3.42 (m, 2 H), 3.11–2.99 (m, 2 H), 2.76–2.66 (m, 2 H), 2.59 (t, J=8.0, 2 H), 1.94–1.90 (m, 4 H), 1.67–1.58 (m, 4 H), 1.40–1.27 (m, 12 H); $^{13}$C NMR (CDCl$_3$, 75.46 MHz) δ 158.42, 150.65, 147.55, 142.79, 128.77, 128.29, 128.12, 125.47, 123.43, 122.78, 120.20, 115.79, 49.48, 35.89, 34.08, 31.71, 31.41, 29.41, 29.37, 29.28, 29.23, 26.86, 24.73, 23.01, 22.76.

EXAMPLE 23

Pharmacological Activity

Representative compounds of formula II in their salt form were tested in vitro for selectivity and potency as cholinesterase inhibitors. Rat brain homogenate prepared in 10 ml/g 10 mM Tris, pH 7.4, plus 1% Triton X-100 was used as a source of AChE; rat serum was the source of BChE. AChE was assayed spectrophotometrically with acetylthiocholine as substrate, in the presence of $10^{-4}$ M ethopropazine as BChE inhibitor (G. L. Ellman et al., *Biochem. Pharmacol.*, 7, 88 (1961). BChE was assayed similarly with butyrylthiocholine as substrate and $10^{-5}$ M BW284C51 as AChE inhibitor. The measured IC$_{50}$ values for inhibitions of AChE and a related enzyme, butyrylcholinesterase (BChE), are listed in Table 1.

TABLE I

IC$_{50}$ of THA and Analogs
for Inhibition of AChE and BChE.

| | | rat brain AChE | IC$_{50}$ (nM) rat serum BChE | Selectivity[†] |
|---|---|---|---|---|
| | THA | 250 | 40 | 0.2 |
| Class 1. | 1a | 0.2 | 315 | 1369.6 |
| | 1b | 0.5 | 216 | 432.0 |
| | 1c | 0.5 | 202 | 404.0 |
| | 1d | 2.0 | 360 | 180.0 |
| Class 2. | 2a | 1500 | NA* | NA |
| | 2b | 1500 | 500 | 0.3 |
| | 2c | 520 | 800 | 1.5 |
| | 2d | 360 | 1000 | 2.8 |
| | 2e | 220 | 2000 | 9.1 |
| | 2f | 3000 | 10,000 | 3.3 |
| | 2g | 3000 | NA | NA |

*NA: Not available
[†]Selectivity: IC$_{50}$ BChE divided by IC$_{50}$ for AChE.

Figure 5A:
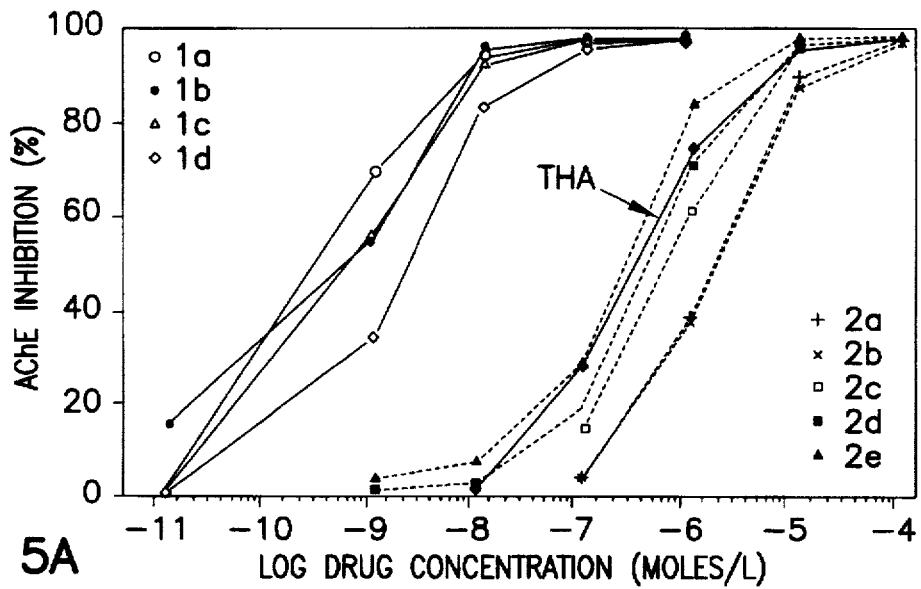
FIG. 5 depicts plots of the inhibition of rat AChE, BChE, and normalized $IC_{50}$ (AChE inhibition) by compounds of the invention.
Figure 5B:
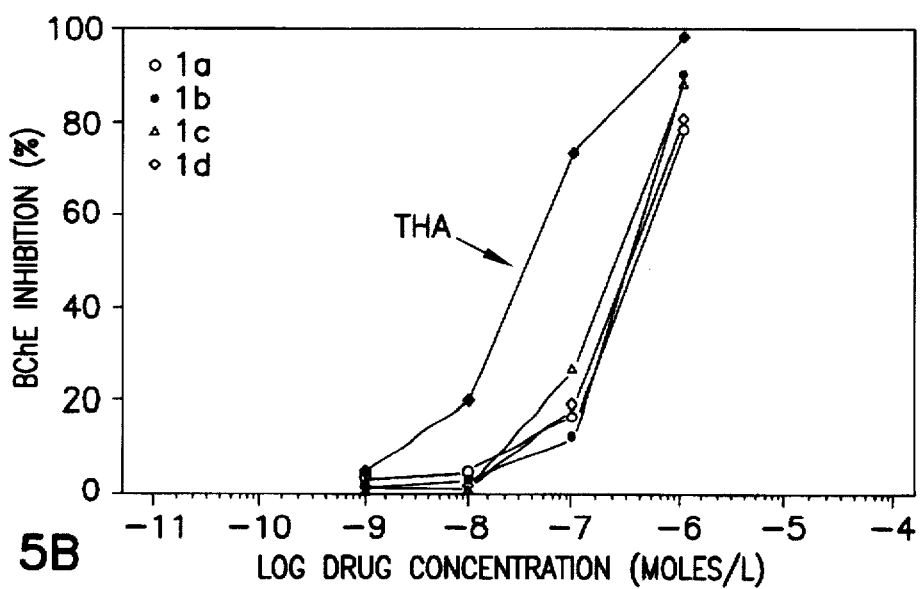
Figure 5C:
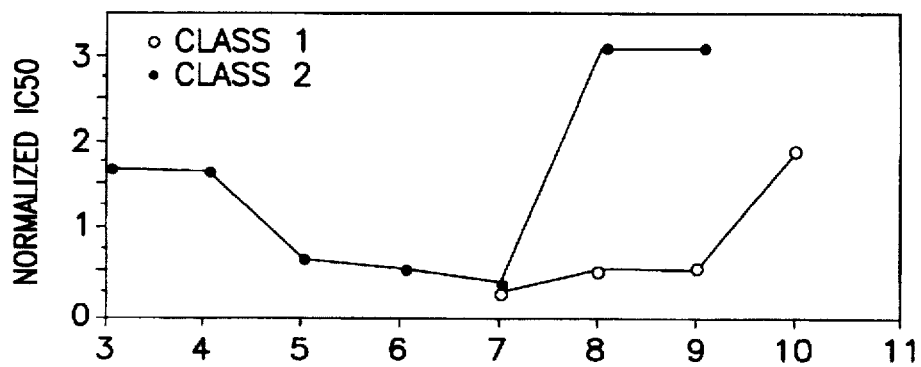
Figure 6A:
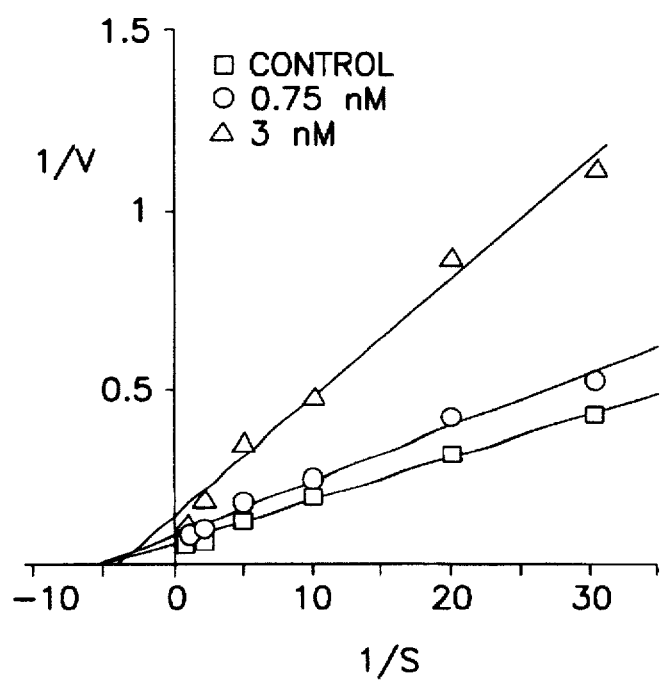
FIG. 6 depicts plots of the substrate kinetics of human brain ACHE inhibition by 1a (Panel A) and THA (Panel B).
Figure 6C:
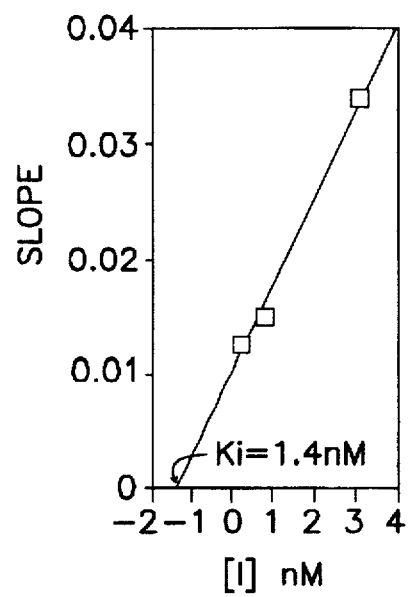
Figure 6B:
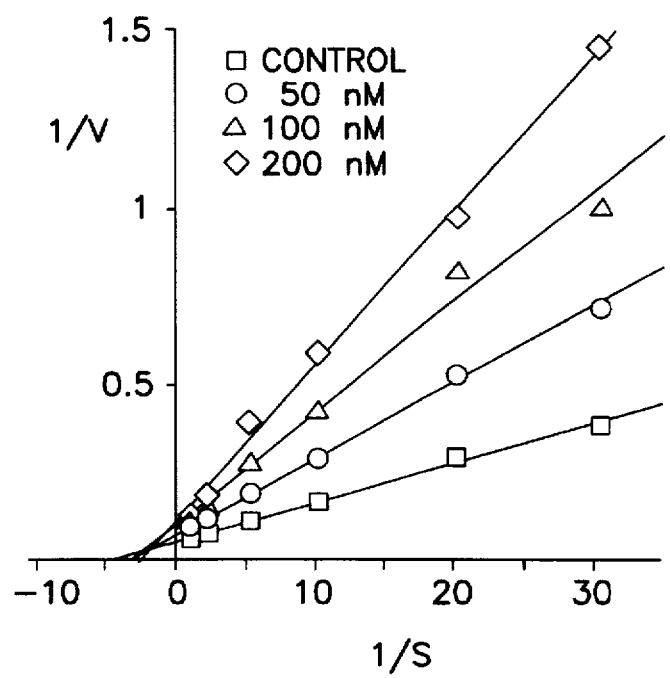
Figure 6D:
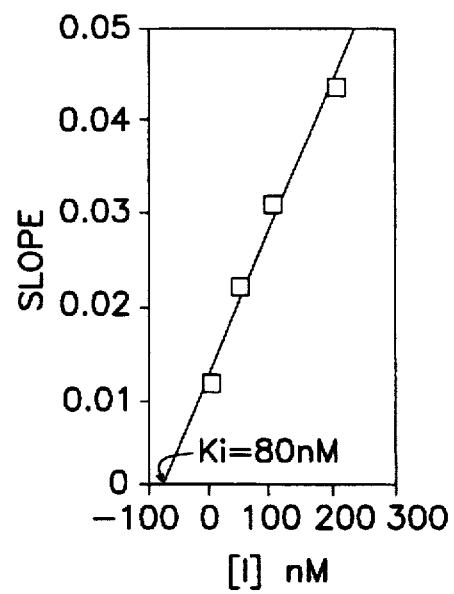

As compared with THA, compound 1a proved 1000 times more potent and 7000 times more selective in inhibiting rat brain AChE (FIG. 5). Inhibitory potency was inversely related to the length of the alkylene chain. Optimal chain length for this series was reached in compound 1a, with 7 methylene groups between THA residues.

For a rigorous test of the compounds' anticholinesterase properties, the substrate-kinetics of enzyme inhibition were examined in a highly purified preparation of human brain AChE. AChE was highly purified from autopsied human cerebellum by affinity chromatography on procainamide Sepharose, essentially as described by D. de la Hoz et al., Life Sci. 39, 195 (1986). Enzyme activity was measured as described supra, except that acetylthiocholine concentration was varied. Reciprocal velocity was plotted against reciprocal substrate concentration in the presence of varying concentrations of compound 1a (FIG. 6, Panel A) and THA (FIG. 6, Panel B). On the right, K$_i$ values for the two AChE inhibitors were taken from the negative X-intercepts of the slope replots. According to the reciprocal slope-replot procedure of I. H. Segel, Enzyme Kinetics, 170 (1975), class 1 analogs, like THA itself, produced a linear mixed type of enzyme inhibition. The calculated K$_i$ for compound 1a was 1.4 nM. This value is well below the 80 nM K$_i$ determined for THA in the same AChE preparation. It does appear that THA inhibits human AChE more readily than rat AChE, at which its K$_i$ is nearly micromolar. Even so, the results conclusively demonstrate the superior potency of bisfunctional analogs as inhibitors of AChE in the mammalian brain.

Inhibition curves of "class 2" analogs (FIG. 5) showed that compound 2e was the most potent: further decrease or increase of chain length weakened AChE inhibition. This result confirmed that the chain length of bis-aromatic THA analogs is an important determinant of potency. In particular, a spacing of 7 methylene units between THA and toluene residues of the class 2 compounds was consistently associated with maximal effect on the catalytic function of AChE. Thus, modification of the spacer chain can serve as a molecular "switch" for the property of AChE inhibition.

It is striking that, when tested against rat brain AChE, compound 2e and THA were nearly equipotent inhibitors and were weaker than compound 1a. The dramatic increase in inhibitory potency conferred by the additional THA residue in compound 1a may reflect facilitation in binding.

In addition, lipophilicity of compounds 1 and 2 was confirmed to be increased over THA. This is evidenced by that these compounds in their salt form were not completely dissolved in the ethanol-containing aqueous solution until the percentage of EtOH was raised to 40%, while THA in its salt form was readily dissolved in the ethanol-free aqueous solution. The results of these biological evaluations demonstrate that the present compounds can be used for one or more of the above-mentioned applications, because of (i) their greatly improved potency and selectivity to ACHE inhibition; (ii) their increased hydrophobicity, and (iii) their efficient and economical synthesis.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of the general formula (I):

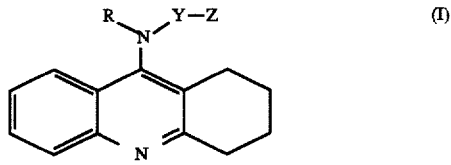

wherein R is H or (C$_1$-C$_4$)alkyl, Y is (C$_4$-C$_{15}$)alkylene or (C$_4$-C$_{15}$)alkylene N(R) and Z is 1,2,3,4-tetrahydroacridin-9-yl; or a pharmaceutically acceptable salt thereof.

2. A compound of claim 1 wherein R is H.

3. A compound of claim 1 wherein Y is (C$_4$-C$_{12}$)alkylene or (C$_4$-C$_{12}$)alkylene N(R).

4. The compound of claim 3 wherein Y is —(CH$_2$)$_n$— or —(CH$_2$)$_n$—N(R)—, wherein n is 6–10.

5. 1,ω-n-alkylene-bis-9,9'-amino-1,2,3,4-tetrahydroacridine, wherein n is 7–10.

6. A pharmaceutical composition comprising an effective AChE or BChE inhibitory amount of a compound of claim 1 in combination with a pharmaceutically acceptable carrier.

7. The composition of claim 6 which is adapted for oral administration.

8. The composition of claim 6 which is adapted for parenteral administration.

9. An insecticidal or parasiticidal composition comprising an effective AChE inhibitory amount of a compound of claim 1 in combination with a carrier vehicle.

10. The composition of claim 9 wherein the carrier vehicle is a finely divided inert solid.

11. The composition of claim 9 wherein the carrier vehicle is a liquid vehicle.

12. A method for inhibiting cholinesterase activity in a human afflicted with a condition which is ameliorated by cholinesterase inhibition comprising administering an amount of a compound of claim 1 effective to inhibit said activity.

13. The method of claim 12 wherein the cholinesterase is AChE.

14. The method of claim 12 wherein the cholinesterase is BChE.

* * * * *